United States Patent [19]
Friedman et al.

[11] Patent Number: 5,372,932
[45] Date of Patent: Dec. 13, 1994

[54] ANALYTICAL ELEMENT AND METHOD FOR THE DETERMINATION OF A SPECIFIC BINDING LIGAND USING A 4-HYDROXY OR 4-ALKOXYARYLACETAMIDE AS STABILIZER

[75] Inventors: Alan E. Friedman; Linda A. Mauck; Thomas R. Kissel, all of Rochester, N.Y.

[73] Assignee: Eastman Kodak Company, Rochester, N.Y.

[21] Appl. No.: 995,608

[22] Filed: Dec. 22, 1992

[51] Int. Cl.$^5$ ................ G01N 33/543; G01N 21/76
[52] U.S. Cl. .................... 435/7.9; 435/7.4; 435/7.92; 435/7.93; 435/7.94; 435/7.95; 435/28; 435/970; 422/52; 422/56; 422/57; 422/68.1; 252/700
[58] Field of Search ............ 252/700; 435/6, 7.9, 435/7.92, 7.93, 7.94, 7.95, 28, 962, 963, 967, 968, 970, 7.4; 422/56, 57, 52, 68.1, 69

[56] References Cited

U.S. PATENT DOCUMENTS

| | | | |
|---|---|---|---|
| 3,492,349 | 1/1970 | Doyle et al. | 564/223 |
| 3,651,141 | 3/1972 | Galantay | 564/158 |
| 3,746,741 | 7/1973 | Hubele | 560/34 |
| 4,265,909 | 5/1981 | Jollow et al. | 514/629 |
| 4,288,592 | 9/1981 | Rauhut et al. | 544/159 |
| 4,424,150 | 1/1984 | Khanna | 530/300 |
| 4,504,413 | 8/1985 | Khanna | 435/188 |
| 4,524,217 | 6/1985 | Davenport et al. | 564/223 |
| 4,598,044 | 7/1986 | Kricka et al. | 435/28 |
| 4,605,754 | 8/1986 | Khanna | 560/19 |
| 4,746,607 | 5/1988 | Mura et al. | 435/25 |
| 4,828,983 | 5/1989 | McClune | 435/7.92 |
| 4,828,983 | 5/1993 | McClune | 435/6 |
| 4,973,752 | 11/1990 | Fruchey | 564/223 |
| 4,999,457 | 3/1991 | Fruchey | 564/223 |
| 5,024,935 | 6/1991 | McClune et al. | 435/7.1 |
| 5,047,318 | 9/1991 | Snyder et al. | 435/5 |
| 5,051,356 | 9/1991 | Warren et al. | 435/7.34 |

OTHER PUBLICATIONS

Daly et al, *Biochem. Pharm.*, 17, pp. 31–36 (1968).
Calder et al, *Aust. J. Chem.*, 29, pp. 1801–1808 (1976).
Calder et al, *Chem.-Biol. Interactions*, 8, pp. 87–90 (1974).

*Primary Examiner*—Esther M. Kepplinger
*Assistant Examiner*—Lora M. Green
*Attorney, Agent, or Firm*—J. Lanny Tucker

[57] ABSTRACT

A dry analytical element can be used to sensitively and rapidly detect a wide variety of specific binding ligands in either a competitive binding or sandwich assay format. The assays are carried out using a peroxidase-labeled immunoreactant. The peroxidase label is stabilized with a 4-hydroxy or 4-alkoxyarylacetamide which is located in one or more zones of the element. Not only is the label stabilized with the stabilizer, but the assay is more sensitive.

18 Claims, No Drawings

ANALYTICAL ELEMENT AND METHOD FOR THE DETERMINATION OF A SPECIFIC BINDING LIGAND USING A 4-HYDROXY OR 4-ALKOXYARYLACETAMIDE AS STABILIZER

FIELD OF THE INVENTION

This invention relates to analytical elements and methods for using them to detect specific binding ligands in fluid samples. In particular, it relates to the stabilization of peroxidase-labeled immunoreactants in such analytical elements.

BACKGROUND OF THE INVENTION

There is a continuing need in medical practice and research, and in analytical and diagnostic procedures for rapid and accurate determinations of chemical and biological substances which are present in various fluids, such as biological fluids. For example, the presence of proteins, hormones, drugs, viruses, microorganisms, narcotics and steroids must be determined rapidly and accurately for effective research, diagnosis and treatment.

A wide variety of analytical methods have been developed in recent decades to detect the noted substances. The methods have become highly reliable and in some instances, suitable for automation, as well as suitable for use in kit form. Most of such methods rely on what are known in the art as "specific binding reactions" between a substance to be detected (identified herein as a "specific binding ligand" or "ligand") and a corresponding "receptor" which recognizes and reacts with the ligand specifically. Most well known specific binding reactions are between immunoreactants (in "immunoassays"), such as antibodies with antigens or antibodies with haptens, but others are also known (such as avidin with biotin).

In general, immunoassays can provide a qualitative or quantitative determination (or both) of the presence or absence (or quantity) of a specific antigen, antibody or antigen-antibody complex. In one form of immunoassay known as a "competitive binding immunoassay", a labeled analog of the ligand to be determined is placed in competition with a fixed amount of an appropriate antibody which can react with both the ligand and the ligand analog. The label on the analog can be appropriately detected in its "free" or complexed (that is, reacted) form. Such detection will then tell the user how much ligand is in the sample being tested.

In an alternative immunoassay format known as a "sandwich" immunoassay or immunometric assay, the ligand is contacted with two or more receptor molecules which bind to the ligand at different epitopic sites. One receptor is typically appropriately labeled and the other is either immobilized on a solid substrate, or is capable of being immobilized thereon. The amount of ligand is directly proportional to the amount of bound complex among the ligand and the two receptors.

Immunoassays have been traditionally carried out in solution, or in test devices where fluids are removed in some fashion from the reagents participating in the assay. Dry analytical elements and their use for immunoassays are described in numerous publications, including U.S. Pat. No. 4,258,001 (Pierce et al), U.S. Pat. No. 4,670,381 (Frickey et al), WO 82/2601 (published Aug. 5, 1982), EP-A-0 051 183 (published May 12, 1982) and EP-A-0 066 648 (published Dec. 15, 1982).

Improved dry analytical elements and their use in immunoassays are described in U.S. Ser. No. 938,460 (filed Aug. 31, 1992 by Belly et al) in which enzyme labels are utilized for detection. Peroxidase is the preferred enzyme label. Such elements allow for the detection of analytes present in very low concentrations using a particular wash technique to separate unbound reactants from bound (or complexed) immunoreactants.

In the immunoassays carried out in the dry analytical elements using peroxidase as the label, the stability of the peroxidase is highly important since any change in its concentration critically affects assay sensitivity. In the assays described in U.S. Ser. No. 938,460, 4'-hydroxyacetanilide is used as an electron transfer agent to enhance the rate of signal production when the enzyme label reacts with its substrate.

While 4'-hydroxyacetanilide effectively enhances assay sensitivity, it has been observed that the stability of the peroxidase label is less than desired in dry analytical elements. There is a need to have an element which demonstrates the sensitivity provided by 4'-hydroxyacetanilide, but which has improved enzyme stability.

SUMMARY OF THE INVENTION

The problems noted with previous dry analytical elements and immunoassays are overcome with an analytical element for the determination of a specific binding ligand, the element comprising:

a porous spreading zone, and one or more additional zones which are in fluid contact with the porous spreading zone, the element containing in at least one of the zones:

a peroxidase-labeled immunoreactant which is capable of specifically reacting with either of a specific binding ligand of interest or its receptor, or an unlabeled immunoreactant which is capable of specifically reacting with either the specific binding ligand of interest or its receptor, and the element further containing in at least one of the zones, a peroxidase stabilizer having the structure(I):

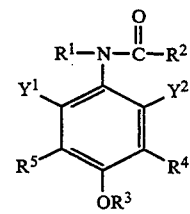

structure (II):

structure (III):

or structure (IV):

-continued

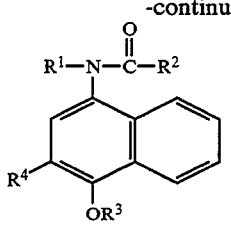

wherein $R^1$ is hydrogen or alkyl of 1 to 4 carbon atoms, $R^2$ is hydrogen, alkyl of 1 to 4 carbon atoms, alkoxyalkyl of 1 to 4 carbon atoms, hydroxyalkyl of 1 to 4 carbon atoms, aminoalkyl of 1 to 4 carbon atoms, haloalkyl of 1 to 4 carbon atoms, or alkenyl of 2 to 5 carbon atoms, $R^3$ is hydrogen or alkyl of 1 to 4 carbon atoms, $R^4$ and $R^5$ are independently hydrogen or an electron withdrawing group having a Hammett sigma value of at least about 0.01, and $Y^1$ and $Y^2$ are independently hydrogen, alkyl of 1 to 4 carbon atoms, or an electron withdrawing group having a Hammett sigma value of at least about 0.01, provided that in structure (I), at least one of $R^4$ and $R^5$ is an electron withdrawing group having a Hammett sigma value of at least about 0.01.

This invention also provides a method for the determination of a specific binding ligand comprising:

A. contacting a fluid sample suspected of containing the specific binding ligand with the analytical element described above, to bring about a separation of the unreacted form of the peroxidase-labeled immunoreactant from the reacted form of the peroxidase-labeled immunoreactant, and B. detecting either the unreacted or reacted form of the peroxidase-labeled immunoreactant as a measure of the specific binding ligand of interest.

The present invention provides a highly sensitive and stabilized peroxidase label for use in the dry analytical element. This element is useful for determining any of a wide variety of specific binding ligands, but particularly for the determination of ligands at low concentrations. The advantage of enzyme stability is obtained by incorporating a peroxidase stabilizer of structure (I), (II), (III) or (IV) noted above in the element. Even greater sensitivity can be achieved in a preferred embodiment by using the peroxidase stabilizer in the element and 4'-hydroxyacetanilide in a wash solution which is applied to the element during the immunoassay to effect separation of unreacted peroxidase-labeled immunoreactant from the reacted form of the peroxidase-labeled immunoreactant.

DETAILED DESCRIPTION OF THE INVENTION

The method of this invention is a specific binding assay, such as an immunoassay, which can be either competitive binding or immunometric as those terms are known in the art. The analyte of interest to be determined is a specific binding ligand, a labeled counterpart is a labeled ligand analog, and a specifically binding reactant with either of them is a receptor.

The present invention is used to advantage to determine low concentrations of ligands in various aqueous liquids, such as human and animal biological fluids, foods, industrial or municipal effluent, and other fluids commonly tested in this manner. Biological fluids which can be tested include, but are not limited to, whole blood, serum, plasma, urine, spinal fluid, lacrimal fluid, synovial fluid, lymphatic fluid, suspensions of tissues or plaque, gingival fluid, vaginal fluid, cranial fluid and other fluids readily apparent to one skilled in the art.

Ligands which can be determined include, but are not limited to, peptides, polypeptides, proteins (such as enzyme, antibodies, lipoproteins and glycoproteins), drugs, narcotics, steroids, toxins and saccharides (such as polysaccharides). Specific binding ligands of particular interest include digoxin, phenytoin, phenobarbital, theophylline, C-reactive protein, human chorionic gonadotropin, thyroid stimulating hormone, a thyronine derivative (such as thyroxine and triiodothyronine), creatine kinase-MB, carbamazepine, gentamicin, tobramicin or vancomicin. The present invention is most useful in the determination of digoxin, phenytoin, phenobarbital and C-reactive protein.

The invention is carried out using an analytical element comprising a porous spreading zone (usually a coated layer) which has suitable porosity for accommodating a test sample (for example 1 to 200 μl), diluted or undiluted. Preferably, the porous spreading zone is isotropically porous, which property is provided by interconnected spaces among the particles, fibers or other physical components of the zone. By isotropically porous is meant that fluids are uniformly spread throughout the zone. Useful absorbent materials for such zones are water-insoluble and maintain their structural integrity during the assay. Conventional materials are described, for example, in U.S. Pat. No. 3,992,158 (Przybylowicz et al), U.S. Pat. No. 4,258,001 (noted above), U.S. Pat. No. 4,292,272 (Kitazima et al) and U.S. Pat. No. 4,430,436 (Koyama et al). The preferred porous spreading zones are prepared from organo-polymeric particles and a polymeric adhesive in a coherent, three-dimensional structure, as described in U.S. Pat. No. 4,258,001 (noted above).

There are one or more other zones in the element, all of which are in fluid contact with the porous spreading zone. By "fluid contact" is meant that fluid can readily move from one zone to another. Such additional zones (preferably coated layers) include subbing, reagent, radiation blocking zones and are composed of one or more hydrophilic binder materials as are known in the art (such as gelatin, acrylamide polymers and vinylpyrrolidone polymers). Some zones may be water-insoluble while others may be water-soluble.

The zones of the element can be self-supporting, but preferably, they are disposed on a suitable dimensionally stable, chemically inert support. Preferably, the support is nonporous and transparent to electromagnetic radiation. A support of choice should be compatible with the intended mode of detection (for example, transmission or reflectance spectroscopy). Useful support materials include, but are not limited to, paper, metal foils, polystyrenes, polyesters, polycarbonates and cellulose esters.

In at least one of the zones of the element, is a peroxidase stabilizer having any of structures (I):

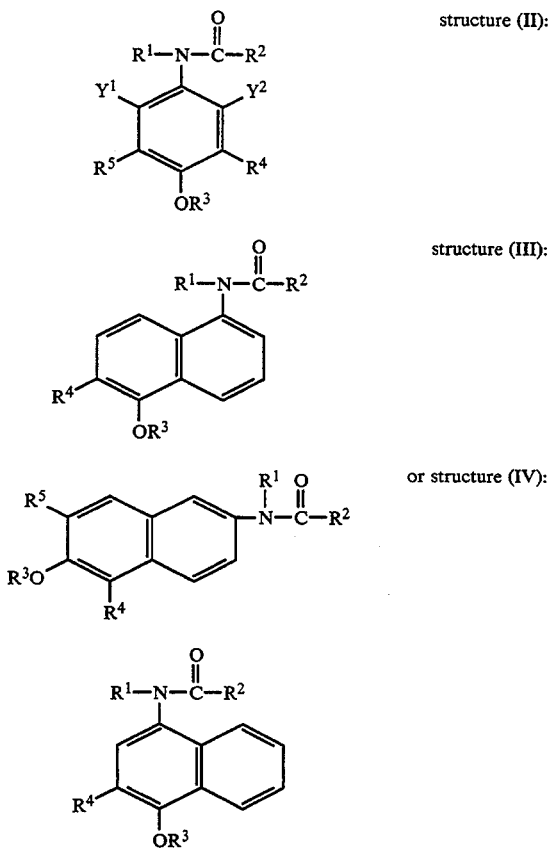

structure (II):

structure (III):

or structure (IV):

wherein $R^1$ is hydrogen or alkyl of 1 to 4 carbon atoms (such as methyl, ethyl, isopropyl, hydroxymethyl, aminomethyl and methoxymethyl). Preferably, $R^1$ is hydrogen.

In structure (I), (II), (III) and (IV), $R^2$ is hydrogen, alkyl of 1 to 4 carbon atoms (such as methyl, ethyl isopropyl, t-butyl and isobutyl), alkoxyalkyl of 1 to 4 carbon atoms (such as methoxymethyl and methoxyethyl), hydroxyalkyl of 1 to 4 carbon atoms (such as hydroxymethyl, 1-hydroxyethyl, 2-hydroxyethyl and 2,3-dihydroxypropyl), aminoalkyl of 1 to 4 carbon atoms (such as aminomethyl, 2-aminoethyl, 3-aminopropyl, 2,4-diaminobutyl, methylaminomethyl, 2-dimethylaminoethyl and 4-aminobutyl), haloalkyl of 1 to 4 carbon atoms (such as chloromethyl, bromomethyl, 2-chloroethyl, 1,1-dichloromethyl, 1,1,1-trichloromethyl, 2,2,2-trichloroethyl and 3-chloropropyl), or alkenyl of 2 to 5 carbon atoms (such as ethenyl, 1-propenyl, isopropenyl and 2-butenyl). Preferably, $R^2$ is hydrogen, methyl or ethenyl.

$R^3$ is hydrogen or alkyl of 1 to 4 carbon atoms (such as methyl, ethyl, isopropyl, t-butyl, n-butyl and isobutyl). Preferably, $R^3$ is hydrogen or methyl.

$R^4$ and $R^5$ are independently hydrogen or an electron withdrawing group having a Hammett sigma value of at least about 0.01, and preferably at least about 0.3. Hammett sigma values are calculated in accordance with standard procedures described, for example, in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (fluoro, bromo, chloro or iodo), trihalomethyl (for example, trifluoromethyl or trichloromethyl), carbonyl, carbamoyl, sulfonyl, sulfamoyl, esters and others readily apparent to one skilled in the art. Preferred electron withdrawing groups are halo (such as chloro or bromo) and cyano. Chloro and cyano are more preferred electron withdrawing groups, and chloro is most preferred for either of $R^4$ and $R^5$.

$Y^1$ and $Y^2$ are independently hydrogen, alkyl of 1 to 4 carbon atoms (as defined above for $R^2$), or an electron withdrawing group as defined above for $R^4$ and $R^5$. Preferably, $Y^1$ and $Y^2$ are independently hydrogen, methyl or ethyl, and most preferably, each is hydrogen or methyl.

In the foregoing structure (I), at least one of $R^4$ and $R^5$ must be an electron withdrawing group as defined above. In foregoing structures (II), (III) and (IV), at least one of $R^2$, $R^4$ and $R^5$ can be an electron withdrawing group, but this is not required.

Representative peroxidase stabilizers having structure (I) include:
3'-chloro-4'-hydroxyacetanilide,
3',5'-dichloro-4'-hydroxyacetanilide,
3',5'-dichloro-4'-hydroxy-2'-methylacetanilide,
3'-fluoro-4'-hydroxyacetanilide,
3',5'-difluoro-4'-hydroxyacetanilide,
3'-bromo-4'-hydroxyacetanilide,
3',5'-dibromo-4'-hydroxyacetanilide,
3'-cyano-4'-hydroxyacetanilide,
3',5'-dicyano-4'-hydroxyacetanilide,
N-methyl-N-(3-chloro-4-hydroxyphenyl)acetamide,
N-(3- chloro-4-hydroxyphenyl)methacrylamide,
N-(3-chloro-4-methoxyphenyl)acetamide,
N-(3-chloro-4-hydroxyphenyl)-2-chloroacetamide,
N-(3-chloro-4-hydroxyphenyl)-2,2-dichloroacetamide,
N-(3-chloro-4-hydroxyphenyl)-2,2,2-trichloroacetamide,
N-(3-chloro-4-hydroxyphenyl)-2-hydroxyacetamide,
N-(3-chloro-4-hydroxyphenyl)-2-methoxyacetamide, and
N-(3-chloro-4-hydroxyphenyl)-2-aminoacetamide.

Representative peroxidase stabilizers of structure (II) include:
N-(5-hydroxy-1-naphthyl)acetamide,
N-(5-hydroxy-6-fluoro-1-naphthyl)acetamide,
N-(5-hydroxy-6-chloro-1-naphthyl)acetamide,
N-(5-hydroxy-6-cyano-1-naphthyl)acetamide,
N-methyl-N-(5-hydroxy-1-naphthyl)acetamide,
N-methyl -N-(5-hydroxy-6-chloro-1-naphthyl)acetamide,
N-(5-methoxy-1-naphthyl)acetamide,
N-(5-methoxy-6-chloro-1-naphthyl)acetamide,
N-(5-hydroxy-1-naphthyl)-2-chloroacetamide,
N-(5-hydroxy-1-naphthyl)-2,2-dichloroacetamide,
N-(5-hydroxy-6-chloro-1-naphthyl)-2,2-dichloroacetamide,
N-(5-hydroxy-1-naphthyl)-2,2,2-trichloroacetamide,
N-(5-hydroxy-6-chloro-1-naphthyl)-2,2,2-trichloroacetamide,
N-(5-hydroxy-1-naphthyl)-2-hydroxyacetamide,
N-(5-hydroxy-6-chloro-1-naphthyl)-2-hydroxyacetamide,
N-(5-hydroxy-1-naphthyl)-2-methoxyacetamide,
N-(5-hydroxy-6- chloro-1-naphthyl)-2-methoxyacetamide,
N-(5-hydroxy-1-naphthyl)-2-aminoacetamide, and N-(5-hydroxy-6-chloro-1-naphthyl)-2-aminoacetamide.

Representative peroxidase stabilizers of structure (III) include:

N-(6-hydroxy-2-naphthyl)acetamide,
N-(6-hydroxy-5-fluoro-2-naphthyl)acetamide,
N-(6-hydroxy-7-fluoro-2-naphthyl)acetamide,
N-(6-hydroxy-5,7-difluoro-2-naphthyl)acetamide,
N-(6-hydroxy-5-chloro-2-naphthyl)acetamide,
N-(6-hydroxy-5,7-dichloro-2-naphthyl)acetamide,
N-(6-hydroxy-7-bromo-2-naphthyl)acetamide,
N-(6-hydroxy-5,7-dibromo-2-naphthyl)acetamide,
N-(6-hydroxy-5-cyano-2-naphthyl)acetamide,
N-(6-hydroxy-5,7-dicyano-2-naphthyl)acetamide,
N-methyl-N-(6-hydroxy-5-chloro-2-naphthyl)acetamide,
N-methyl-N-(6-hydroxy-7-chloro-2-naphthyl)acetamide,
N-methyl-N-(6-hydroxy-5,7-dichloro-2-naphthyl)acetamide,
N-(6-methoxy-2-naphthyl)acetamide,
N-(6-methoxy-5-chloro-2-naphthyl)acetamide,
N-(6-methoxy-5,7-dichloro-2-naphthyl)acetamide,
N-(6-hydroxy-2-naphthyl)-2-chloroacetamide,
N-(6-hydroxy-7-chloro-2-naphthyl)-2-chloroacetamide,
N-(6-hydroxy-2-naphthyl)-2,2-dichloroacetamide,
N-(6-hydroxy-7-chloro-2-naphthyl)-2,2,2-trichloroacetamide,
N-(6-hydroxy-2-naphthyl)-2-hydroxyacetamide,
N-(6-hydroxy-5-chloro-2-naphthyl)-2-methoxyacetamide,
N-(6-hydroxy-2-naphthyl)-2-aminoacetamide, and
N-(6-hydroxy-5,7-dichloro-2-naphthyl)-1-aminoacetamide.

Representative peroxidase stabilizers of structure (IV) include:

N-(4-hydroxy-1-naphthyl)acetamide,
N-(4-hydroxy-3- fluoro-1-naphthyl)acetamide,
N-(4-hydroxy-5-chloro-1-naphthyl)acetamide,
N-methyl -N-(4-hydroxy-3-chloro-1-naphthyl)acetamide,
N-(4-methoxy-1-naphthyl)acetamide,
N-(4-hydroxy-1-naphthyl)-2-chloroacetamide,
N-(4-hydroxy-3- chloro-1- naphthyl)-2-chloroacetamide,
N-(4-hydroxy-1-naphthyl)-2,2-dichloroacetamide,
N-(4-hydroxy-5-chloro-1-naphthyl)-2-methoxyacetamide,
N-(4-hydroxy-5-chloro-1-naphthyl)-2-aminoacetamide, and
N-(4-hydroxy-3-chloro-1-naphthyl)-2-aminoacetamide.

The preferred peroxidase stabilizers are 3',5'-dichloro-4'-hydroxyacetanilide, 3'-chloro-4'-hydroxyacetanilide and 3',5'-dichloro-4'-hydroxy-2'-methylacetanilide.

The peroxidase stabilizers can be prepared generally from known starting materials as follows:

In general, the halogenated compounds of Structures (I)-(IV) are prepared by halogenation of the known precursor anilide (for example, 4'-hydroxy-, or alkoxy-, acetanilide, or an anilide of naphthalene) with a known halogenating agent such as sulfuryl chloride, sulfuryl bromide, or the free halogen in the presence of acid. Where the desired precursor is not available, an appropriately substituted phenol or naphthol can be nitrated by mild nitration using known techniques (for example, with nitric acid in a solvent such as glacial acetic acid) followed by hydrogenation, typically over platinum or paladium to produce the amine (see *J. Am. Chem. Soc.* 49, 1093, 1927). The amine is then acylated, for example, by condensation with the desired acylating agent such as an anhydride (for example, acetic anhydride) or an acid chloride such as acrylic acid chloride, to produce the anilide. Suitable acylation procedures are also described by Challis et al, *The Chemistry of Amides*, pp. 731–857, Intersciences Publishing, New York, 1970. If the selected starting materials do not already provide the requisite electron withdrawing groups, the resulting anilide can be conveniently halogenated as described above. Alternatively, the aromatic ring of the amine precursor to the anilide can be alkylated, acylated or nitrated at the $R^4$ or $R^5$ (or both) positions using known techniques.

The peroxidase stabilizer identified above by structure (I), (II), (III) or (IV) is present in the element in a minimum amount of about 0.05 $g/m^2$. Preferably, it is present in an amount of from about 0.15 to about 0.5 $g/m^2$, and the total amount can be in the same zone, or it can be divided and put into more than one zone. Additionally, a plurality of stabilizers can be used in one or more of the zones of the element.

Also within the element of this invention is a peroxidase-labeled immunoreactant which is capable of specifically reacting with either the specific binding ligand of interest or its receptor. In competitive binding immunoassays, the labeled immunoreactant is usually a labeled analog of the specific binding ligand. In sandwich assays, the labeled immunoreactant can be a labeled receptor for the ligand, or it can be a labeled molecule which specifically binds to the receptor (such as a labeled anti-antibody).

Such labeled immunoreactants can be prepared using any of a number of known procedures including that described by Yoshitake et al, *Eur. J. Biochem.* 101, 395, 1979 and in U.S. Pat. No. 5,106,732 (Kondo et al). By "peroxidase" is meant any peroxidative substance (enzymatic or otherwise) which catalyzes the oxidation of a substrate, such as a leuco dye, to produce the appropriate signal. Microbial, fungal and plant peroxidases are preferred with horseradish peroxidase being most preferred. The amount of peroxidase-labeled immunoreactant can vary widely due to the amount of the other components used in the reaction and the suspected amount of analyte in the test sample. Generally, the amount present in the element is at least about 1 $\mu g/m^2$, with from about 2 to about 100 $\mu g/m^2$ being preferred.

The element of this invention further contains an unlabeled immunoreactant which is capable of specifically reacting with either the specific binding ligand of interest or its receptor. In competitive binding immunoassays, this immunoreactant is generally a receptor (such as antibody) to the ligand. In sandwich immunoassays, the unlabeled immunoreactant can be a receptor for the ligand, or a binding molecule for the receptor. In preferred embodiments, the immunoreactant is an antibody specific to the ligand.

The unlabeled immunoreactant is located in any zone of the element, except it is generally not located in the same zone as the peroxidase-labeled immunoreactant. Thus, those two components of the element are kept separated in some fashion until the assay has begun. They may be separated by locating them in different zones of the element, or they may be in the same zone, but one is encapsulated with a material that releases the immunoreactant when the assay is begun. Preferably, the immunoreactants are kept in separate zones (or layers).

It is also preferred that the unlabeled immunoreactants are immobilized on suitable particles that are dispersed throughout a zone of the element. Such particles can be composed of any suitable material including, but not limited to, glass, iron oxides, ceramics, organic synthetic or naturally occurring polymers, and have an average particle size of from about 0.01 to about 10 μm. Preferably, the particles are prepared from synthetic polymers and have suitable surface groups for adsorption or covalent attachment of the immunoreactant molecules. A wide variety of such materials are known in the art such as those described in U.S. Pat. No. 4,828,978 (Warren III et al), U.S. Pat. No. 4,997,772 (Sutton et al), U.S. Pat. No. 5,147,777 (Sutton et al), U.S. Ser. No. 81,206 (filed on Aug. 3, 1987 by Sutton et al, or corresponding EP-A-0 323,692) abandoned in favor of continuation U.S. Ser. No. 07/742,198 (filed Aug. 5, 1991), now U.S. Pat. No. 5,177,023, and references noted therein.

Particularly useful polymeric particles are those prepared from ethylenically unsaturated polymerizable monomers having reactive carboxy, 2-substituted ethylsulfonyl or vinylsulfonyl groups, particularly as described in the two Sutton et al patents noted in the preceeding paragraph.

With the use of peroxidase as the label in the method of this invention, there is a need to bring the peroxidase-labeled immunoreactant in contact with hydrogen peroxide and the appropriate reagents to produce a colorimetric or chemiluminescent signal. Useful reagents for providing a colorimetric signal include, but are not limited, imidazole or triarylmethane leuco dyes, such as those described in U.S. Pat. No. 4,089,747 (Bruschi) and references noted therein, EP-A-0 122 641 (published Oct. 24, 1984), Japanese Patent Publication No. 58(1983)-045557 and U.S. Pat No. 4,670,385 (Babb et al).

The triarylimidazole leuco dyes described in the Bruschi patent are preferred for generating a colorimetric signal in the practice of this invention. Such leuco dyes generally have the structure (V):

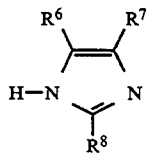

wherein $R^6$, $R^7$ and $R^8$ are independently an organic group such that at least one of them is an o- or p-hydroxy-substituted aryl group of up to 18 carbon atoms in the aromatic ring, and the other two groups being aryl groups chosen such that the imidazole oxidation potential is within the range of from about −70 to about +100 mV as measured by cyclic voltammetry against a standard calomel electrode using a carbon based electrode. Oxidation potential measurements can be made according to conventional electrochemical techniques (see for example, Sawyer et al, *Experimental Electrochemistry for Chemists,* John Wiley & Sons, New York, 1974).

As used in the definition of the leuco dyes, "aryl" is meant to include aromatic hydrocarbon groups such as phenyl, naphthyl or anthryl, tolyl, xylyl and other substituted aromatic groups. The number of carbon atoms refers to the total nuclear carbon atoms as well as those in the substituents. At least one of the $R^6$, $R^7$ and $R^8$ groups has an ortho or para electron donating substituent such as an alkyoxy (−OR′) wherein R′ is alkyl of 1 to 8 carbon atoms (such as methyl, ethyl, isopropyl, t-butyl, hexyl, chloromethyl or methoxymethyl), or a dialkylamino wherein alkyl is as just defined. Useful leuco dyes can be purchased from commercial sources or prepared using known technology.

Particularly useful triarylimidazole leuco dyes are:
2-(3,5-dibromo-4-hydroxyphenyl)-4,5-diphenylimidazole,
3-(3-bromo-5-methoxy-4-hydroxyphenyl) -4,5-bis (4-methoxyphenyl)imidazole,
4,5-bis(4-dimethylaminophenyl)-2-(4-hydroxyphenyl)imidazole,
4,5-bis(4-dimethylaminophenyl)-2-(4-hydroxy-3-methoxyphenyl)imidazole,
2-(4-hydroxyphenyl)-4,5-bis(4-methoxyphenyl)imidazole, and
4,5-bis(4-methoxyphenyl)-2-(3,5-dimethoxy-4-hydroxyphenyl)imidazole.

The leuco dyes described above can be prepared using known materials and procedures, and some are available commercially.

Diazonium and tetrazolium salts useful as reagents in the practice of this invention must be those capable of reacting in the presence of peroxidase and an oxidant to produce a chromophore. A diazonium salt is generally an organic salt of a compound having a diazonium radical.

Particularly useful diazonium salts include, but are not limited to, those having the following structure (VI):

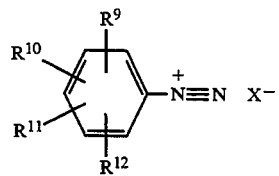

wherein $R^9$, $R^{10}$, $R^{11}$ and $R^{12}$ are independently hydrogen, halo (such as chloro, bromo or iodo), alkyl of 1 to 12 carbon atoms (such as methyl, ethyl, isopropyl, t-butyl, sec-butyl, n-butyl, pentyl, octyl, isononyl and dodecyl), nitro, cyano, alkoxy of 1 to 6 carbon atoms (such as methoxy, ethoxy, pentoxy, isopropoxy, t-butoxy and hexoxy), aryloxy of 6 to 10 carbon atoms in the aromatic ring, including aryloxy substituted with alkoxy and alkyl as defined above (such as phenoxy, naphthoxy, tolyloxy and p-nitrophenoxy), aryl of 6 to 10 carbon atoms (such as phenyl, naphthyl, n-methylphenyl, m-ethoxyphenyl, p-cyanophenyl and o-methoxyphenyl), acyl of 1 to 12 carbon atoms (such as acetyl, propionyl, benzoyl and butyryl), and substituted or unsubstituted carbamoyl or sulfamoyl (such as carbamoyl, sulfamoyl, N,N-dimethylcarbamoyl and N,N-diethylsulfamoyl). Preferably, $R^9$, $R^{10}$, $R^{11}$ and $R^{12}$ are independently hydrogen, methyl, chloro, N,N-diethylsulfamoyl, nitro or methoxy.

In addition, any two of these radicals at adjacent positions on the ring can be taken together to represent a 6- to 10-membered fused aromatic ring system, including both heterocyclic or carbocyclic fused aromatic rings. Such rings can include carbon, nitrogen, oxygen or sulfur atoms in the ring structure. Preferably, 6- to 10-membered carbocyclic ring systems are formed in this manner.

In the salt noted above, $X^-$ represents any suitable anion which does not inhibit or act as a substrate for peroxidases, such as halide (for example, chloride, bromide and fluoride), tetrafluoroborate, nitrate, perchlorate, p-toluenesulfonate and others readily apparent to one skilled in the art.

Representative useful diazonium salts include, but are not limited to, N',N'-diethyl-4-methoxymetanilamide diazonium salt (known as Fast Red-ITR salt), 4-chloro-2-methylbenzendiazonium salt (known as Fast Red TR salt), diazotized 2-methoxy-5-chloroaniline (known as Fast Red RC salt) and diazotized 5-nitro-2-amino-1-methoxybenzene (known as Fast Red B).

Tetrazolium salts are organic salts in which the organic portion contains one or two tetrazole rings, generally with aryl substituents at various positions. Tetrazolium salts having two tetrazole rings can be formed to provide a biphenyl nucleus with a tetrazole ring in each of the 4- and 4'- positions of the biphenyl nucleus.

Many useful diazonium and tetrazolium compounds are described for example, in U.S. Pat. No. 3,905,872 (Forgione), U.S. Pat. No. 4,772,553 (Fujii et al), U.S. Pat. No. 4,892,817 (Pawlak) and U.S. Pat. No. 4,892,833 (Weiss et al) and Japanese Publication 63/088,000 (published Apr. 19, 1988). Many diazonium and tetrazolium salts useful herein are available from a number of commercial sources, and those not readily available can be readily prepared by a skilled organic chemist using available reagents and known procedures.

Chemiluminescent signals can be obtained using a variety of known reagents. A preferred chemiluminescent signal generating reagent is a 2,3-dihydro-1,4-phthalazinedione derivative (identified herein as "DPD"). Any free or conjugated 2,3-dihydro-1,4-phthalazinedione derivative that can be converted to an excited state in a chemiluminescent reaction and then returns to a non-excited state with the emission of light, is useful in the practice of this invention. A considerable number of such compounds are known in the art, including those described in U.S. Pat. No. 4,598,044 and *Chemiluminescence in Organic Chemistry*, Gundermann and McCapra, Springer-Verlag, Berlin, 1987, pages 204–207. Such compounds are generally known as "luminol type hydrazides" and include phthalic hydrazides, naphthalene-1,2-dicarboxylic acid hydrazides, anthracene-2,3-dicarboxylic acid hydrazides, phenathrene-1,2-dicarboxylic acid hydrazides, fluorene-1,2-dicarboxylic acid hydrazides, benzo[g,h,i]perylene-1,2-dicarboxylic acid hydrazides, coronene-1,2-dicarboxylic acid hydrazides, and others readily apparent to one skilled in the art.

In particular, the DPD is defined by the structure (V):

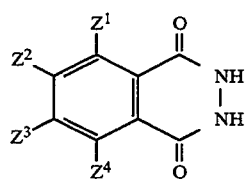

wherein $Z^1$, $Z^2$, $Z^3$ and $Z^4$ are independently hydrogen, alkyl of 1 to 6 carbon atoms (such as methyl, ethyl, isopropyl, t-butyl, sec-pentyl and hexyl), alkenyl of 2 to 6 carbon atoms [such as ethenyl, 1-propenyl, isobutenyl, 2-(N,N-diisopropylamino)vinyl, 2-(N,N-diisobutylamino)vinyl, 2-(N,N-diisopentylamino)vinyl and 2-hexenyl], hydroxy, alkoxy of 1 to 6 carbon atoms (such as methoxy, ethoxy, isopropoxy, t-butoxy and hexoxy), carboxy, amino [including amino substituted with alkyl or alkanoyl, such as methylamino, ethylamino, amido (for example, acetamido and hexanamido), dimethylamino, diethylamino and diisobutylamino], conjugated aminoalkenyl (for example, as defined below) or aminoaryl [including substituted aminoaryl, such as p-(N,N-dimethylamino)phenyl, p-(N,N-diethylamino)phenyl and 5-amino-2,3-dihydro-1,4-phthalazinedion-8-yl (also known as luminyl)].

At least one of $Z^1$ and $Z^2$ is amino (including substituted amino, as defined above), conjugated aminoalkenyl (including substituted aminoalkenyl as described above) or aminoaryl [such as p-(N,N-dimethylamino)phenyl, p-(N,N-diethylamino)phenyl and 5-amino-2,3-dihydro-1,4-phthalazinedion-8-yl]. As used herein, "conjugated aminoalkenyl" refers to a monovalent group capable of electron resonance from the amino group through the alkenyl group to the aromatic ring of the phthalazinedione where it is substituted, and includes for example, a dialkylaminovinyl group [such as 2-(N,N-diisopropylamino)vinyl, 2-(N,N-diisobutylamino)vinyl and 2-(N,N-diisopentylamino)vinyl], and dialkylaminobutadienyl groups, such as 4-(N,N-diethylamino)-1,3-butadien-1-yl.

Alternatively, any adjacent two, adjacent three or all of $Z^1$, $Z^2$, $Z^3$ and $Z^4$ (that is, combinations of two or three adjacent groups, or all four groups) can be taken together to form a fused ring system containing one or more aromatic rings. Such fused rings can be substituted with one or more hydroxy, amino (substituted or unsubstituted as described above) or alkoxy of 1 to 4 carbon atoms (such as methoxy, ethoxy and isopropoxy). Preferably, such fused rings are substituted with one or more primary, secondary or tertiary amines, hydroxy or alkoxy as described above.

Representative useful DPD compounds include, but are not limited to, luminol, isoluminol, N-(4-aminobutyl)-N-ethylisoluminol hemisuccinimide, N-(6-aminohexyl)-N-ethylisoluminol, N-ethylisoluminol and 7-dimethylaminonaphthalene-1,2-dicarboxylic acid hydrazide. Luminol (5-amino-2,3-dihydro-1,4-phthalazinedione) and isoluminol (6-amino-2,3-dihydro-1,4-phthalazinedione) are preferred, and luminol is most preferred.

Other useful classes of DPD compounds are described in the Gundermann and McCapra publication noted above, and include substituted or unsubstituted phthalic acid hydrazides, anthracene-2,3-dicarboxylic acid hydrazides, phenathrene dicarboxylic acid hydrazides, fluorene-1,2-dicarboxylic acid hydrazides, benzo[g,h,i]perylene-1,2-dicarboxylic acid hydrazides and coronene-1,2-dicarboxylic acid hydrazides, such as those illustrated by the following structures:

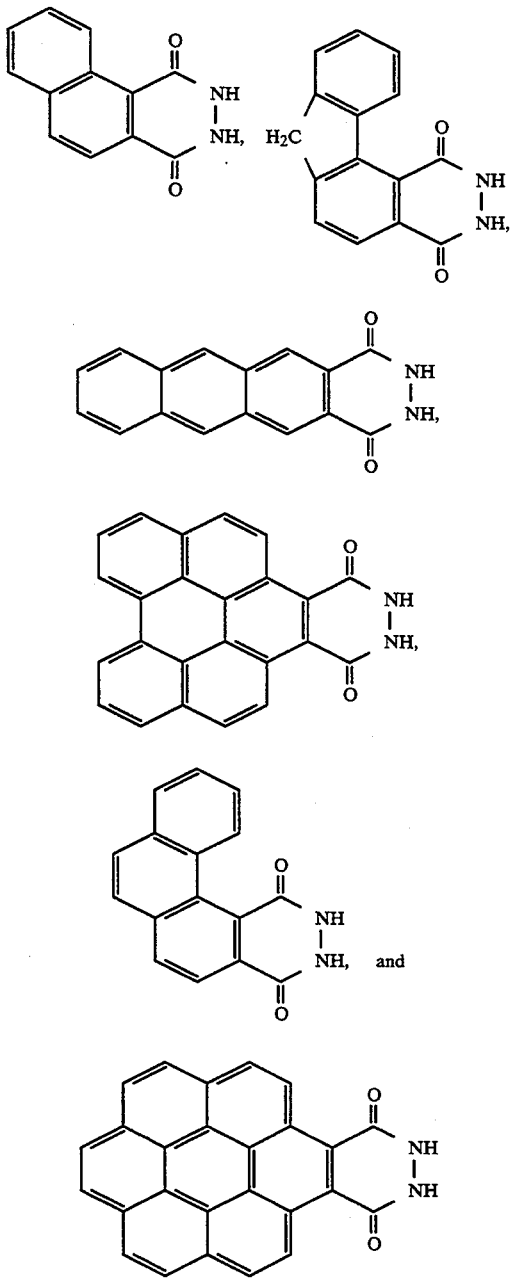

The DPD compounds noted above can be obtained commercially, or be prepared using conventional starting materials and known procedures.

In a preferred embodiment of this invention, a multilayer analytical element for the determination of a specific binding ligand comprises a nonporous support having thereon, in fluid contact:

a first reagent buffer layer, a subbing layer comprising an unlabeled immunoreactant capable of reacting with either a specific binding ligand of interest or its receptor, a porous spreading layer containing a reagent capable of providing a colorimetric or chemiluminescent signal in the presence of hydrogen peroxide and peroxidase, and contiguous to the porous spreading layer, a second reagent layer containing a peroxidase-labeled immunoreactant which is capable of reacting with the specific binding ligand of interest or its receptor, the element further comprising, in one or more of the foregoing layers, a peroxidase stabilizer having structure (I), (II), (III) or (IV).

In a more preferred embodiment, the second reagent layer is located directly over the porous spreading layer.

The reagent for providing a colorimetric or chemiluminescent signal can also be located in the subbing layer instead of the porous spreading layer.

The elements of this invention can include a variety of addenda in appropriate zones as are known in the art to aid in manufacture, fluid spreading, absorbance of unwanted radiation and receptor stability.

The element of this invention can be prepared using conventional coating procedures and equipment as are described in considerable art (including gravure, curtain, hopper and other coating techniques). The elements can be configured in a variety of forms, including elongated tapes or any desired width, sheets, slides or chips. Further, the method of this invention can be manual or automated using appropriate analytical equipment and procedures. Generally, the method includes contacting the reagents in the element by spotting a test sample (for example, 1 to 200 $\mu$l) on the porous spreading zone. The movement of fluid within the element effectively mixes the reagents for the reactions to take place.

After sample application, the element is exposed to any conditioning, such as incubation, heating or other procedure, that may be desirable to quicken or otherwise facilitate forming the appropriate specific binding complexes in the various zones of the element. While in some instances, a suitable signal can be obtained without effective separation of the reacted and unreacted forms of the peroxidase-labeled immunoreactant, it is preferred that the forms be separated within a zone of the element, as is typical in what are known as heterogeneous immunoassays. Thus, a signal can be better read in a defined region of the zone.

Applying a wash solution (from about 5 to about 200 $\mu$l)to the element is the preferred procedure for affecting this separation. The wash solution can be applied in any suitable manner known in the art, but preferably, it is applied at a continuous metered rate, for example of up to 10 $\mu$l/sec and most preferably, at about 1 $\mu$l/sec. However, any rate and method of wash solution application can be used as long as the porous spreading zone readily absorbs the fluid during application.

The wash solution can comprise any known components known in the art for this purpose, and could merely be distilled water or a common buffer solution. Preferably, the wash solution includes a peroxide (such as hydrogen peroxide), a surfactant, a metal chelating agent and an electron transfer agent. Useful electron transfer agents include, but are not limited to, 4'-hydroxyacetanilide and other phenols and anilines described in U.S. Pat. No. 4,828,983 (McClune). A preferred electron transfer agent is 4'-hydroxyacetanilide.

Alternatively, a peroxidase stabilizer as described in any of structures (I), (II), (III) and (IV) above, can also be used in the wash solution as an electron transfer agent.

The wash solution can optionally include a reagent for providing a chemiluminescent signal, such as a DPD as defined above.

The amounts of the components of the wash solution are within the skill of an artisan, but generally the electron transfer agent is present in an amount of at least about 0.1 molar, and preferably from about 0.5 to about 10 molar.

The element of this invention can be used in a variety of assay formats to provide chemiluminescent or colorimetric signal in response to the reacted or unreacted form of the peroxidase-labeled immunoreactant.

The following examples are illustrative of the invention and not to be limiting. All percentages are by weight, unless otherwise indicated.

MATERIALS AND METHOD FOR EXAMPLES

The following dry analytical elements were prepared using conventional procedures and used in the examples:

| Element 1: | Element Structure | Dry Coverage (g/m$^2$) |
|---|---|---|
| Gravure Reagent Layer | Digoxin-horseradish peroxidase | $1.2 \times 10^{-5}$ |
| | Bovine serum albumin | $2.15 \times 10^{-4}$ |
| | 4'-Hydroxyacetanilide | $3.25 \times 10^{-4}$ |
| | 3-(N-morpholino)propane-sulfonic acid buffer (pH 7) | $4.5 \times 10^{-3}$ |
| | Polyacrylamide | $1.08 \times 10^{-3}$ |
| | 4,5-Dihydroxy-3-(6,8-disulfo-2-naphthylazo)-2,7-naphthalene-disulfonic acid, sodium salt | $2.69 \times 10^{-2}$ |
| Spreading Layer | Poly(vinyltoluene-co-methacrylic acid) (98:2 weight ratio) beads (30 µm average diameter) | 130 |
| | Poly(methyl acrylate-co-sodium 2-acrylamido-2-methylpropanesulfonate-co-2-acetoacetoxyethyl methacrylate) (90:4:6 weight ratio) | 2.583 |
| | N-[tris(hydroxymethyl)-methyl]-2-aminoethane-sulfonic acid buffer (pH 7) | 0.219 |
| | Dimedone | 0.5 |
| | Dimethyl sulfoxide | 1.8 |
| | Triarylimidazole leuco dye | 0.2 |
| | 4'-Hydroxyacetanilide | 0.45 |
| | Bovine serum albumin | 1 |
| | Mannitol | 1 |
| | Glycerol | 2 |
| Subbing Layer | Poly (vinylpyrrolidone) | 1.1 |
| | N-[tris(hydroxymethyl)-methyl]-2-aminoethane-sulfonic acid buffer (pH 7) | 0.1 |
| | TRITON ™ X-100 nonionic surfactant | 0.02 |
| | Anti-digoxin monoclonal antibodies covalently attached to poly [styrene-co-p-(2-chloroethyl-sulfonylmethyl)styrene] (95:5 weight ratio) beads (0.5 µm average diameter) | 0.015 |
| Reagent Layer | Hardened gelatin | 10.15 |
| | N-[tris(hydroxymethyl)-methyl]-2-aminoethane-sulfonic acid buffer (pH 7) | 4.58 |
| | 4'-Hydroxyacetanilide | 0.15 |
| | TRITON ™ nonionic surfactant | 0.02 |
| | Polyethylene terephthalate Support | |

ELEMENT 2

This element was like Element 1 except that 3'-5'-dichloro-4'-hydroxyacetanilide is used in place of 4'-hydroxyacetanilide in similar quantities,

ELEMENT 3

This element was like Element 1 except that it contained no peroxidase-labeled digoxin analog.

ELEMENT 4

This element was like Element 2 except that it contained no peroxidase-labeled digoxin analog,

ELEMENT 5

This element was like Element 1 except that poly(N-isopropylacrylamide-co-methacrylic acid-co-N,N'-methylenebisacrylamide) (80:10:10 weight ratio) was used as the subbing layer binder instead of poly(vinylpyrrolidone), and it contained no peroxidase-labeled digoxin analog.

ELEMENT 6

This element was like Element 5 except that it did contain peroxidase-labeled digoxin analog.

ELEMENT 7

This element was like Element 6 except that it contained 3',5'-dichloro-4'-hydroxyacetanilide as the stabilizer instead of 4'-hydroxyacetanilide.

ELEMENT 8

This element was like Element 5 except that it contained 3',5'-dichloro-4'-hydroxyacetanilide as the stabilizer instead of 4'-hydroxyacetanilide.

Elements 2, 4, 7 and 8 are elements prepared according to the practice of this invention, while Elements 1, 3, 5 and 6 are outside the scope of this invention.

The peroxidase-labeled digoxin analog used in the examples was prepared by the procedures and from reagents described in U.S. Ser. No. 558,919, filed Jul. 27, 1990 by Detty and Danielson (or corresponding EP-A-0 468 590, published Jan, 29, 1992), and U.S. Ser. No. 564,940, now abandoned, filed Jul. 27, 1990 by Danielson and Detty (or corresponding to EP-A-0 468 591, published Jan. 29, 1992).

Anti-digoxin monoclonal antibodies were attached to poly[styrene-co-p-(2-chloroethylsulfonylmethyl)-styrene](95:5 weight ratio, 0.5 µm average diameter) beads using the procedures described in U.S. Ser. No. 742,198, filed Aug. 5, 1991 as a CIP of abandoned 81,206 (filed Aug. 3, 1987 by Sutton and Danielson, identified above), now U.S. Pat. No. 5,177,023.

Poly(vinyl pyrrolidone) was obtained from GAF and had an average molecular weight of about 360,000. TRITON ™ X-100 nonionic surfactant is available from Union Carbide. All other reagents and components used in the elements and methods are either available commercially or readily prepared using conventional starting materials using known procedures.

The rate of signal formation was determined by applying a test sample (11 μl)containing digoxin (either 0.05 or 3.1 ng/ml) in a human serum-based matrix to the element, incubating the element for 5 minutes at 37° C., then applying a wash solution (12 μl). This wash solution contained hydrogen peroxide (0.04%), 4'-hydroxyacetanilide (5 nmolar) and diethylenetriaminepentaacetic acid (10 μmolar) in a sodium phosphate buffered surfactant solution (0.01 molar buffer, pH 6.8). Following application of the wash solution, the element was again incubated at 37° C., and the rate of dye formation measured at 670 nm by reflectance densitometry using conventional equipment.

EXAMPLE 1

Comparison of Element/Label Stability

This example compares the elements of the present invention to those outside this invention and shows the improved stability of the peroxidase label according to the practice of this invention.

Elements 1, 2, 6 and 7 were tested in this example. Duplicates of each of the type of element were frozen immediately after manufacture (identified as "fresh"), others were conditioned at 21° C. and 33% relative humidity for three days and then frozen (identified as "conditioned"). Still other elements were conditioned at 21° C. and 33% relative humidity for 10 days and then frozen (identified as "kept"). Elements treated at all three conditions were thawed and then used to assay two different amounts of digoxin in test samples. Enzyme stability in the element was evaluated by comparing the average % of rate retained as a function of the stabilizer in the element. The "average % of rate retained" was calculated by dividing the "conditioned" rate by the "fresh" rate, or by dividing the "kept rate" by the "conditioned rate".

The assay for digoxin was carried out for each element as described above. Elements 1 and 6 are considered Controls in this example. The results of % rate retained (that is, an indication of peroxidase label stability) is shown in the following Table I. The results indicate the there is a significant improvement in stability with the element of this invention containing a peroxidase stabilizer as described herein.

TABLE I

| Element | % Rate Retained | |
|---|---|---|
| | "Conditioned"/ "fresh" | "Kept"/ "conditioned" |
| 1 | 80 | 87 |
| 2 | 99 | 100 |
| 6 | 90 | 92 |
| 7 | 94 | 99 |

Similar improvements in peroxidase label stability were found using elements designed according to the present invention for the determination of phenytoin and phenobarbital.

EXAMPLE 2

Comparison of Assay Sensitivity

This example compares the sensitivity of the assay carried out using "fresh" elements prepared according to the present invention to the sensitivity achieved with elements outside the scope of this invention. All of the elements noted above were tested for sensitivity, with Elements 1, 3, 5 and 6 being considered as Controls.

Elements 1, 2, 6, and 7 contained the peroxidase-labeled digoxin analog coated within a layer thereof, whereas the other elements did not. Thus, the labeled analog was separately added to Elements 3, 4, 5 and 8 during the assay by applying a test sample (11 μl) of the Labeled analog (1 nmolar) with digoxin (0.05 or 6.3 ng/ml), in a human serum-based matrix. The remaining steps of the assay are as described above.

Sensitivity of the individual assays was determined by looking at the "rate range" which is obtained by subtracting the rate observed at 6.3 ng/ml digoxin from the rate observed at 0.05 ng/ml digoxin. A more sensitive assay exhibits a higher rate range. As the results in Table II below show, the elements of the present invention (with or without coated peroxidase-labeled digoxin) demonstrated greater assay sensitivity.

TABLE II

| Element | Rate Range |
|---|---|
| 3 | 0.0692 |
| 4 | 0.1016 |
| 1 | 0.0516 |
| 2 | 0.0692 |
| 5 | 0.0853 |
| 8 | 0.0972 |
| 6 | 0.0674 |
| 7 | 0.0818 |

The invention has been described in detail with particular reference to preferred embodiments thereof, but it will be understood that variations and modifications can be effected within the spirit and scope of the invention. All patents, patent applications (published or unpublished, domestic or foreign), journal literature, books and other published prior art cited herein are incorporated herein by reference for the teaching therein pertinent to this invention.

We claim:

1. An analytical element for the determination of a specific binding ligand, said element comprising:
    a porous spreading zone, and
    one or more additional zones which are in fluid contact with said porous spreading zone,
    said element containing in at least one of said zones:
    a peroxidase-labeled immunoreactant which specifically binds to a receptor for a specific binding ligand of interest, and
    said element further containing in at least one of said zones, a peroxidase stabilizer having the structure (I):

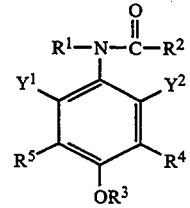

structure (II):

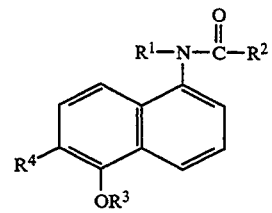

structure (III):

-continued

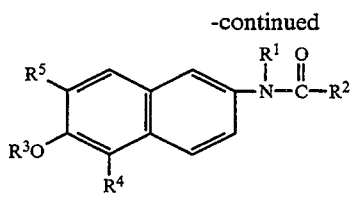 or structure (IV):

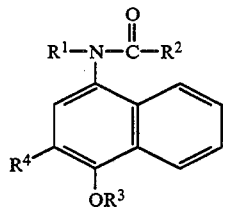

wherein R¹ is hydrogen or alkyl of 1 to 4 carbon atoms,
R² is hydrogen or methyl,
R³ is hydrogen or methyl, and
R⁴ and R⁵ are independently hydrogen, halo or cyano,
Y¹ and Y² are independently hydrogen, alkyl of 1 to 4 carbon atoms, or an electron withdrawing group having a Hammett sigma value of at least about 0.01,
provided that in structure (I), at least one of R⁴ and R⁵ is halo or cyano.

2. The element of claim 1 containing a compound of structure (I) wherein R⁴ and R⁵ are independently chloro or cyano.

3. The element of claim 1 wherein said peroxidase stabilizer is located in at least said porous spreading zone.

4. The element of claim 1 wherein said peroxidase-labeled immunoreactant is a specific binding ligand of interest selected from the group consisting of digoxin, phenytoin, phenobarbital, theophylline, C-reactive protein, human chorionic gonadotropin, thyroid stimulating hormone, a thyronine derivative, carbamazepine, creatine kinase-MB, gentamicin, tobramicin and vancomicin.

5. A multilayer analytical element for the determination of a specific binding ligand, said element comprising a nonporous support having thereon, in fluid contact:
a first reagent or buffer layer,
a subbing layer comprising an unlabeled immunoreactant which specifically binds with a specific binding ligand of interest,
a porous spreading layer containing a reagent capable of providing a colorimetric or chemiluminescent signal in the presence of hydrogen peroxide and peroxidase, and
contiguous to said porous spreading layer, a second reagent layer containing a peroxidase-labeled immunoreactant which specifically binds with a receptor for said specific binding ligand of interest,
said element further comprising, in one or more of said foregoing layers, a peroxidase stabilizer having structure (I):

structure (II):

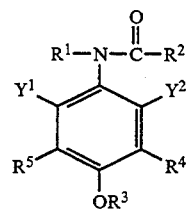

structure (III):

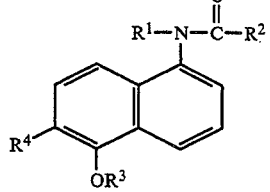

or structure (IV):

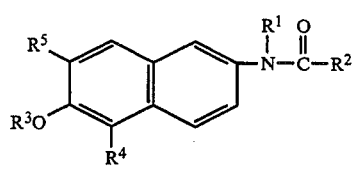

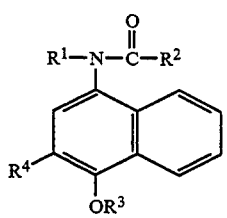

wherein R¹ is hydrogen or alkyl of 1 to 4 carbon atoms,
R² is hydrogen or methyl,
R³ is hydrogen or methyl, and
R⁴ and R⁵ are independently hydrogen, halo or cyano,
Y¹ and Y² are independently hydrogen, alkyl of 1 to 4 carbon atoms, or an electron withdrawing group having a Hammett sigma value of at least about 0.01,
provided that in structure (I), at least one of R⁴ and R⁵ is halo or cyano.

6. The element of claim 5 wherein said porous spreading layer is a beaded spreading layer.

7. The element of claim 5 wherein said peroxidase stabilizer is selected from the group consisting of 3',5'-dichloro-4'-hydroacetanilide, 3'-chloro-4'-hydroxyacetanilide and 3',5'-dichloro-4'-hydroxy-2'-methylacetanilide.

8. The element of claim 5 wherein said unlabeled immunoreactant is an antibody to digoxin, phenytoin, phenobarbital, theophylline, C-reactive protein, a thyronine derivative, carbamazepine, creatine kinase-MB, gentamicin, tobramicin or vancomycin.

9. The element of claim 5 wherein said second reagent layer is located directly over said porous spreading layer.

10. The element of claim 5 further containing in said porous spreading layer, a triarylimidazole leuco dye which provides a dye in the presence of peroxidase and hydrogen peroxide.

11. A method for the determination of a specific binding ligand comprising:

A. contacting a fluid sample suspected of containing said specific binding ligand with an analytical element comprising:
a porous spreading zone, and
one or more additional zones which are in fluid contact with said porous spreading zone,
said element containing in at least one of said zones:
a peroxidase-labeled immunoreactant which specifically binds to a receptor for said specific binding ligand, and
said element further containing in at least one of said zones, a peroxidase stabilizer having the structure (I):

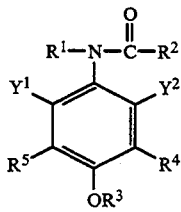

structure (II):

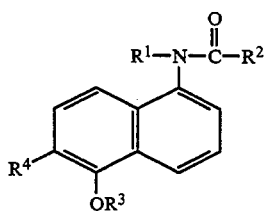

structure (III):

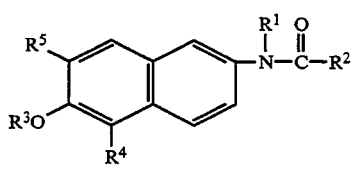

or structure (IV):

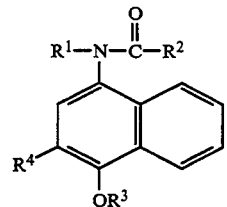

wherein R¹ is hydrogen or alkyl of 1 to 4 carbon atoms,
R² is hydrogen or methyl,
R³ is hydrogen or methyl, and
R⁴ and R⁵ are independently hydrogen, halo or cyano,
Y¹ and Y² are independently hydrogen, alkyl of 1 to 4 carbon atoms, or an electron withdrawing group having a Hammett sigma value of at least about 0.01,
provided that in structure (I), at least one of R⁴ and R⁵ is halo or cyano, B. applying a wash solution to said element to bring about a separation of the unreacted form of said peroxidase-labeled immunoreactant from the reacted form of said peroxidase-labeled immunoreactant, said wash solution comprising a substrate for peroxidase and an electron transfer agent, and C. detecting either said unreacted or reacted form of said peroxidase-labeled immunoreactant as a measure of said specific banding ligand of interest.

12. The method of claim 11 wherein said wash solution is applied to a defined region of said element.

13. The method of claim 11 wherein said wash solution comprises 4'-hydroxyacetanilide as said electron transfer agent.

14. The method of claim 11 wherein said wash solution comprises as said electron transfer agent, a compound having structure (I):

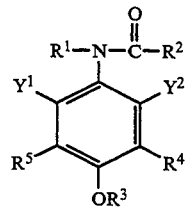

structure (II):

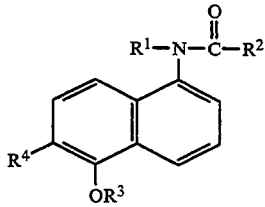

structure (III):

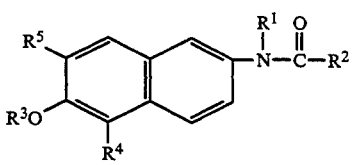

or structure (IV):

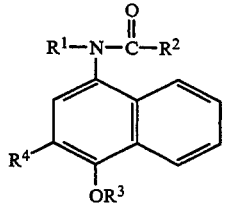

wherein R¹ is hydrogen or alkyl of 1 to 4 carbon atoms,
R² is hydrogen or methyl,
R³ is hydrogen or methyl, and
R⁴ and R⁵ are independently hydrogen, halo or cyano,
Y¹ and Y² are independently hydrogen, alkyl of 1 to 4 carbon atoms, or an electron withdrawing group having a Hammett sigma value of at least about 0.01,
provided that in structure (I), at least one of R⁴ and R⁵ is halo or cyano.

15. The method of claim 11 wherein said reacted form of said peroxidase-labeled immunoreactant is detected from a colorimetric signal.

16. The method of claim 11 wherein said fluid sample is a human or animal biological fluid.

17. An analytical element for the determination of a specific binding ligand, said element comprising:
a porous spreading zone, and
one or more additional zones which are in fluid contact with said porous spreading zone,
said element containing in at least one of said zone:

a peroxidase-labeled immunoreactant which specifically binds to a specific binding ligand of interest, and said element further containing in at least one of said zones, a peroxidase stabilizer having the structure (X):

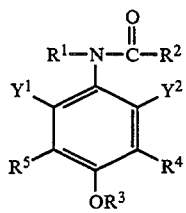

structure (II):

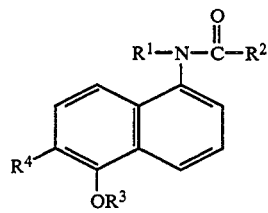

structure (III):

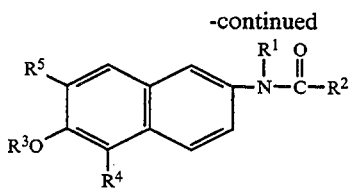

or structure (IV):

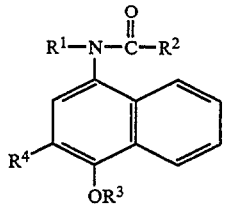

wherein $R^1$ is hydrogen or alkyl of 1 to 4 carbon atoms,
$R^2$ is hydrogen or methyl,
$R^3$ is hydrogen or methyl, and
$R^4$ and $R^5$ are independently hydrogen, halo or
$Y^1$ and $Y^2$ are independently hydrogen, alkyl of 1 to 4 carbon atoms, or an electron withdrawing group having a Hammett sigma value of at least about 0.01,
provided that in structure (I), at least one of $R^4$ and $R^5$ is halo or cyano.

18. The element of claim 12 wherein said peroxidase-labeled immunoreactant is a peroxidase-labeled receptor for said specific binding ligand of interest.

* * * * *